(12) United States Patent
Gogova et al.

(10) Patent No.: US 10,391,069 B2
(45) Date of Patent: *Aug. 27, 2019

(54) SNACKING PRODUCT WITH CAPSAICIN OR ANALOGUE THEREOF

(71) Applicant: ALTRIA CLIENT SERVICES LLC, Richmond, VA (US)

(72) Inventors: Maria Gogova, Richmond, VA (US); Georgios D. Karles, Richmond, VA (US); Gerd Kobal, Sandy Hook, VA (US); Munmaya K. Mishra, Manakin Sabot, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/153,272

(22) Filed: Oct. 5, 2018

(65) Prior Publication Data

US 2019/0038577 A1 Feb. 7, 2019

Related U.S. Application Data

(63) Continuation of application No. 14/206,620, filed on Mar. 12, 2014, now Pat. No. 10,092,528.
(Continued)

(51) Int. Cl.
| | | |
|---|---|---|
| A61K 31/165 | (2006.01) |
| A61K 36/15 | (2006.01) |
| A23P 10/30 | (2016.01) |
| A23L 27/00 | (2016.01) |
| A23L 27/10 | (2016.01) |
| A23L 33/105 | (2016.01) |

(52) U.S. Cl.
CPC .......... *A61K 31/165* (2013.01); *A23L 27/10* (2016.08); *A23L 27/70* (2016.08); *A23L 33/105* (2016.08);
(Continued)

(58) Field of Classification Search
CPC .................................. A61K 31/165
See application file for complete search history.

(56) References Cited

U.S. PATENT DOCUMENTS

| | | |
|---|---|---|
| 5,273,754 A | 12/1993 | Mann |
| 6,201,014 B1 | 3/2001 | Gardiner |

(Continued)

FOREIGN PATENT DOCUMENTS

| | | |
|---|---|---|
| CN | 1682953 A | 10/2005 |
| FR | 2 849 992 | 7/2004 |

(Continued)

OTHER PUBLICATIONS

Xing et al (Journal of Applied Polymer Science, v102, Iss 2, 2006, pp. 1318-1321). (Year: 2006).*

(Continued)

*Primary Examiner* — Benjamin J Packard
(74) *Attorney, Agent, or Firm* — Buchanan Ingersoll & Rooney PC

(57) ABSTRACT

A zero-calorie to near-zero-calorie snacking product that, when consumed, provides a feeling of fullness prior to absorption of energy-providing food, i.e., pre-absorptive satiation is disclosed. The snacking product is based on the stimulation of vagal nerve endings in the gastro-intestinal tract by encapsulated capsaicin. The encapsulation of capsaicin avoids the burning sensation in the mouth which may be objectionable to some consumers.

9 Claims, 6 Drawing Sheets

Prospective Food Consumption as measured by a visual analogue test over time.

Related U.S. Application Data

(60) Provisional application No. 61/779,844, filed on Mar. 13, 2013.

(52) U.S. Cl.
CPC .............. *A23P 10/30* (2016.08); *A61K 36/15* (2013.01); *A23V 2002/00* (2013.01)

(56) References Cited

U.S. PATENT DOCUMENTS

| | | |
|---|---|---|
| 6,812,254 B1 | 11/2004 | Barr et al. |
| 7,867,526 B2 | 1/2011 | Astrup |
| 7,892,582 B2 | 2/2011 | Verneau |
| 2002/0071872 A1 | 6/2002 | McNally et al. |
| 2003/0064122 A1 | 4/2003 | Goldberg et al. |
| 2004/0254142 A1 | 12/2004 | Kovler |
| 2006/0182825 A1 | 8/2006 | Prasad et al. |
| 2006/0194805 A1 | 8/2006 | Bakthavatchalam et al. |
| 2006/0292254 A1 | 12/2006 | More |
| 2007/0209599 A1 | 9/2007 | Block et al. |
| 2008/0268092 A1 | 10/2008 | Dacanay |
| 2010/0048723 A1 | 2/2010 | Yamka et al. |
| 2010/0055253 A1 | 3/2010 | Gautier et al. |
| 2011/0052754 A1 | 3/2011 | Foley |
| 2013/0004601 A1 | 1/2013 | Nielsen et al. |

FOREIGN PATENT DOCUMENTS

| | | |
|---|---|---|
| FR | 2 908 600 | 5/2008 |
| WO | WO 2011/063817 | 6/2011 |

OTHER PUBLICATIONS

Bloomer et al., *Effect of an oral intake of capsaicinoid bedlets on catecholamine secretion and blood markers of lipolysis in healthy adults; a randomized, placebo controlled, double-blind, cross-over study*, 9(72) Lipids in Health and Disease 1-7 (Jul. 15, 2010).

Hughes et al., *The effect of Korean pine nut oil (PinnoThin™) on food intake, feeding behavior and appetite; A double-blind placebo-controlled trial*, 7(1) Lipids in Health and Disease, Biomed Central 1-10 (Feb. 28, 2008).

Inoue et al., *Enhanced Energy Expenditure and Fat Oxidation in Humans with High BMI Scores by the Ingestion of Novel and Non-Pungent Capsaicin Analogues (Capsinoids)*, 71(2) Bioscience, Biotechnology, and Biochemistry 380-389 (Feb. 1, 2007).

Ludy et al., *The Effects of Capsaicin and Capsiate on Energy Balance: Critical Review and Meta-analyses of Studies in Humans*, 37 Chemical Senses 103-121 (Oct. 29, 2011).

Westerterp-Plantenga et al., *Sensory and gastrointestinal satiety effects of capsaicin on food intake*, 29 International Journal of Obesity 682-688 (Jun. 1, 2005).

Yoshioka et al., *Combined effects of red pepper and caffeine consumption on 24 h energy balance in subjects given free access to foods*, 85 British Journal of Nutrition 203-211 (2001).

Yoshioka et al., *Effects of red pepper on appetite and energy intake*, 82 British Journal of Nutrition 115-123 (Jan. 1, 1999).

Capismax—OmniActive http://www.omniactives.com/products/capsim printed on Jun. 11, 2014 (1 Page).

Capismax—OmniActive http://www.omniactives.com/products/capsim printed on Jun. 11, 2014 (2 Pages).

NutritionExpress—Rapidcuts Shredded, http://www.nutritionexpress.com/allmax+nutrition/diet/allmax_nutrition printed on Jun. 11, 2014.

International Search Report issued in PCT/US2014/025399 dated Jul. 8, 2014.

Xing et al., *Study on the Antimicrobial Activities of the Capsaicin Microcapsules*, 102 Journal of Applied Polymer Science 1318-1321 (2006).

Tucci, *Phytochemicals in the Control of Human Appetite and Body Weight*, 3 Pharmaceuticals 748-763 (2010).

Kim et al., *Nanoparticle Formulation for Controlled Release of Capsaicin*, 11 J. of Nanosci. Nanotechnol. 4586-4591 (2011).

Xing et al., *Microencapsulation of Capsaicin by the complex Coacervation of Gelatin, Acacia and Tannins*, 91 Journal of Applied Polymer Science 2669-2675 (2004).

* cited by examiner

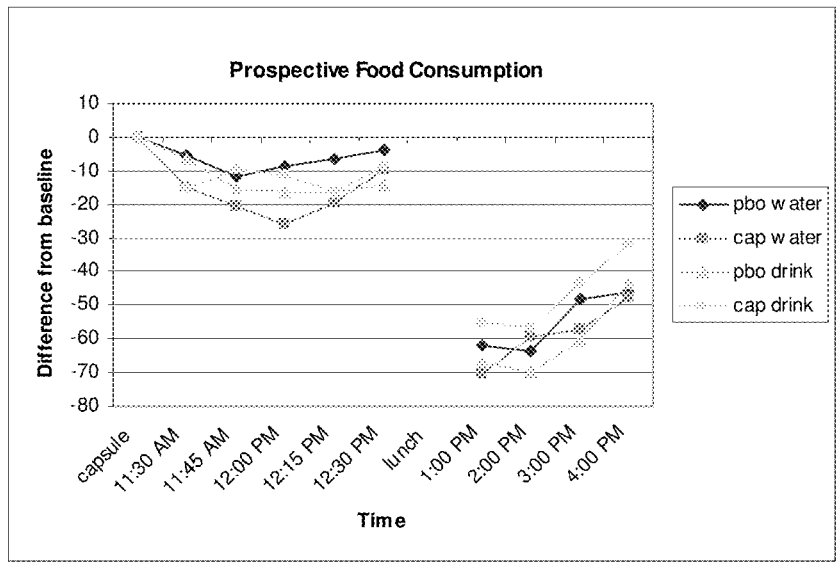
Figure 1: Prospective Food Consumption as measured by a visual analogue test over time.
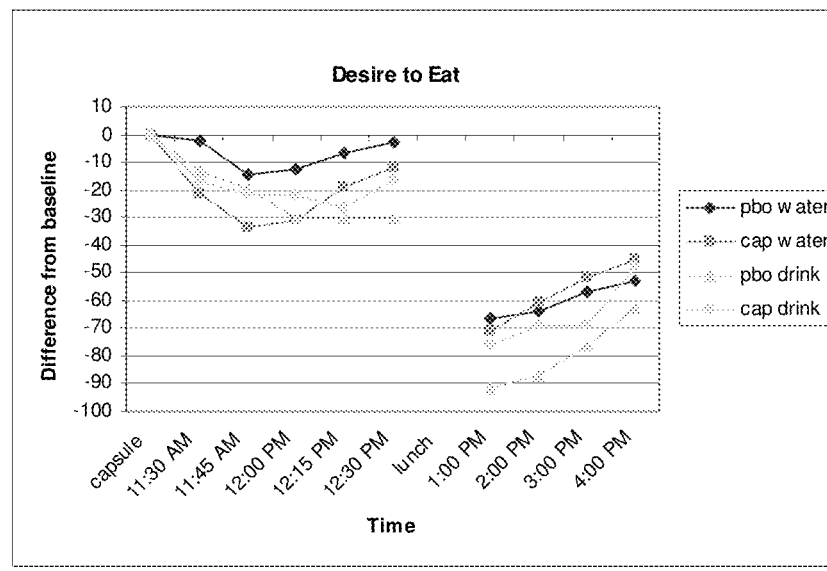
Figure 2: Desire to eat as measured by a visual analogue test over time.

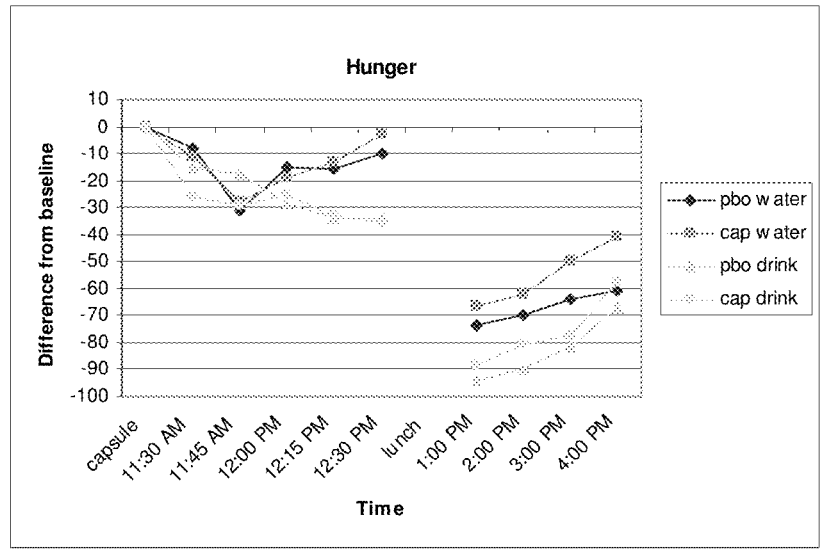
Figure 3: Hunger as measured by a visual analogue test over time.
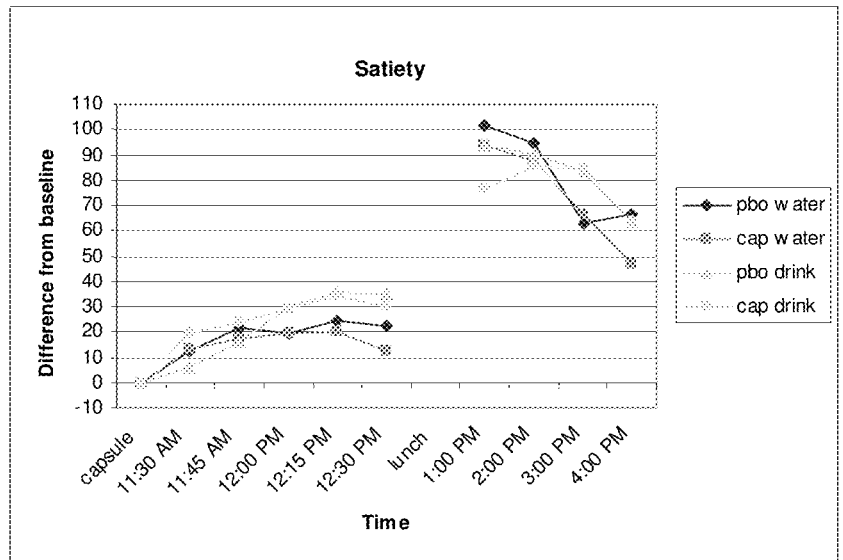
Figure 4: Satiety as measured by a visual analogue test over time.

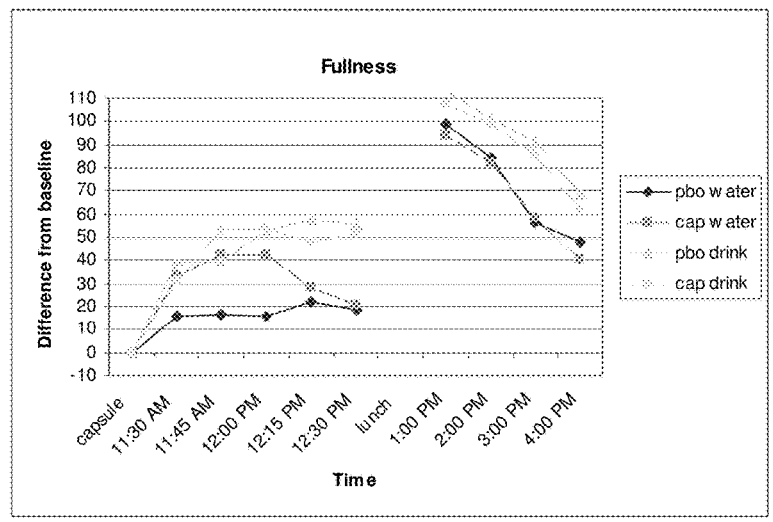
Figure 5: Fullness as measured by a visual analogue test over time.
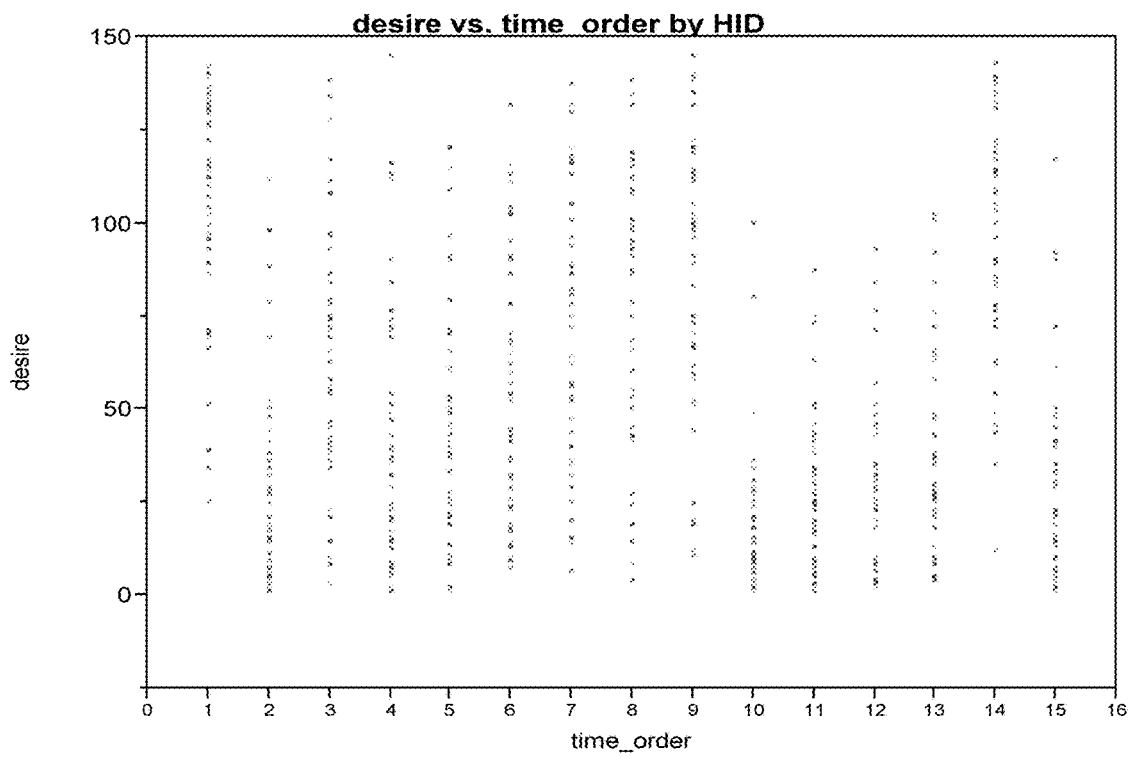
Figure 6: Distribution plot of Desire to Eat ratings. Each point represents an individual participant.

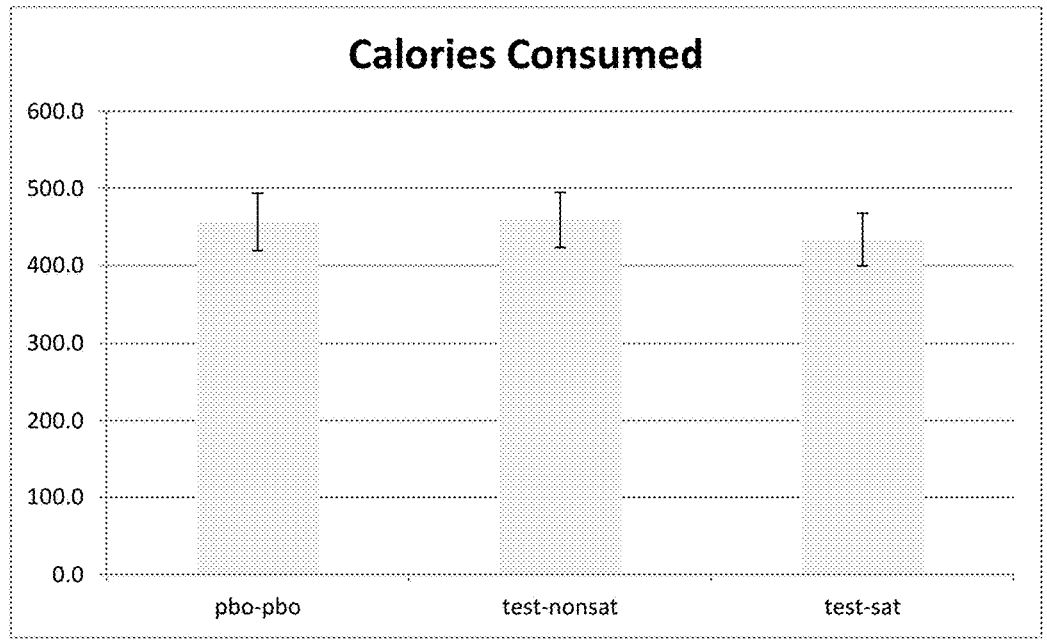
Figure 9: Food intake at lunch. pbo-pbo= placebo; test-nonsat= capsaicin only; test-sat= capsaicin + satiety drink.
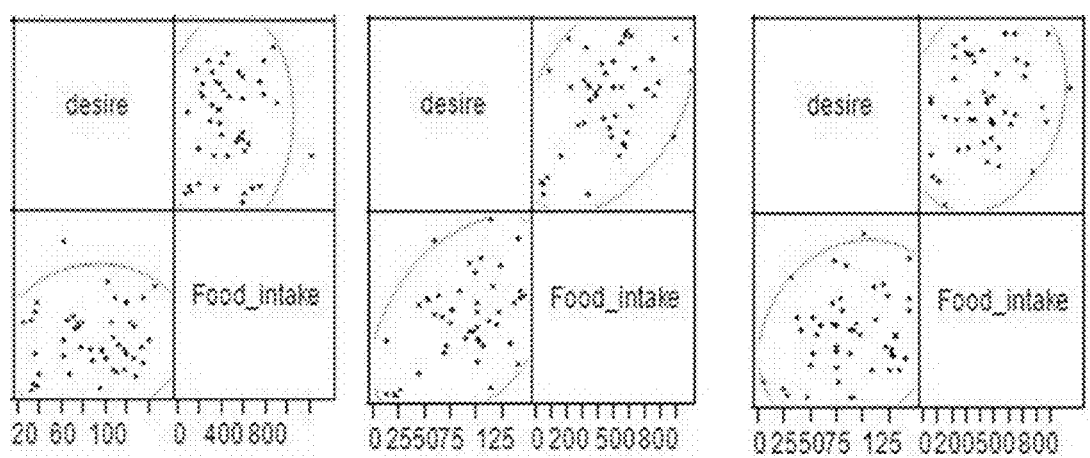
Figure 10: Correlation between food intake and desire to eat. Left= placebo; Middle= capsaicin only; Right= capsaicin + satiety drink.

SNACKING PRODUCT WITH CAPSAICIN OR ANALOGUE THEREOF

CROSS-REFERENCE TO RELATED APPLICATIONS

This application is a continuation application of U.S. patent application Ser. No. 14/206,620, field on Mar. 12, 2014, now allowed, which claims priority to U.S. Provisional Patent Application Ser. No. 61/779,844, field on Mar. 13, 2013. All indicated references are incorporated herein by reference in its entirety for all purposes.

BACKGROUND

Weight loss and dieting are constant struggles for many people. Appetite suppression is one method of controlling food intake, thereby reducing calorie consumption. Appetite suppression is therefore an effective method of weight loss.

Encapsulated capsaicin has the ability to stimulate the vagal nerve endings in the gastro-intestinal tract, thereby causing appetite suppression. Currently-used appetite suppressants include systemic drugs which have many side effects such as dependency, resistance, insomnia, drowsiness, irritability, and/or depression. Accordingly, there is a demand for an appetite suppressant composition which is safe, effective, and without harmful side effects.

SUMMARY

A method for suppressing hunger comprising stimulating vagal nerve endings in the gastrointestinal tract. An additional embodiment is a method for suppressing hunger comprising stimulating vagal nerve endings in the gastrointestinal tract wherein the vagal nerve endings express the transient receptor potential cation channel subfamily receptor V member 1 (TRPV1) receptor. A further embodiment is a method for suppressing hunger comprising stimulating vagal nerve endings in the gastrointestinal tract wherein the vagal nerve endings express the transient receptor potential cation channel subfamily receptor V member 1 (TRPV1) receptor and the cholecystokinin (CCK) receptor.

A method for suppressing hunger comprising stimulating vagal nerve endings in the gastrointestinal tract wherein the stimulation of vagal nerve endings is done by capsaicin, or a capsaicin analogue, or a combination thereof. A further embodiment is a method for suppressing hunger comprising stimulating vagal nerve endings in the gastrointestinal tract wherein the stimulation of vagal nerve endings is done by encapsulated capsaicin, or a capsaicin analogue, or a combination thereof. An additional embodiment is a method for suppressing hunger comprising stimulating vagal nerve endings in the gastrointestinal tract wherein the stimulation of vagal nerve endings is done by micro-encapsulated capsaicin, or a capsaicin analogue, or a combination thereof. Another embodiment is a method for suppressing hunger comprising stimulating vagal nerve endings in the gastrointestinal tract wherein the stimulation of vagal nerve endings is done by administering micro-encapsulated capsaicin, or a capsaicin analogue, or a combination thereof, additionally in combination with Korean Pine Oil.

A snacking product containing a flavor system which stimulates the vagal nerve endings in the gastrointestinal tract and provides pre-absorptive satiation. A further embodiment is a snacking product containing a flavor system which stimulates the vagal nerve endings in the gastrointestinal tract and provides pre-absorptive satiation in which the flavor system comprises encapsulated capsaicin. Another embodiment is a snacking product containing a flavor system which stimulates the vagal nerve endings in the gastrointestinal tract and provides pre-absorptive satiation in which the flavor system comprises encapsulated capsaicin and Korean Pine Oil. An additional embodiment is a snacking product containing a flavor system which stimulates the vagal nerve endings in the gastrointestinal tract and provides pre-absorptive satiation wherein the product is an energy drink, an energy bar, a dietary supplement, a capsule, a pill, or a lozenge. Another embodiment is a snacking product containing a flavor system which stimulates the vagal nerve endings in the gastrointestinal tract and provides pre-absorptive satiation wherein the product is located in a screw cap and is released upon opening of the screw cap.

A method for producing a snacking product containing a flavor system which stimulates the vagal nerve endings in the gastrointestinal tract and provides pre-absorptive satiation comprising combining said flavor system with other ingredients of a snacking product.

BRIEF DESCRIPTION OF FIGURES

FIG. 1 is a graph of prospective food consumption measured by a visual analogue test over time.

FIG. 2 is a graph of desire to eat as measured by a visual analogue test over time.

FIG. 3 is a graph of hunger as measured by a visual analogue test over time.

FIG. 4 is a graph of satiety as measured by a visual analogue test over time.

FIG. 5 is a graph of fullness as measured by a visual analogue test over time.

FIG. 6 is a distribution plot of desire to eat ratings, wherein each point represents an individual participant.

FIG. 9 is a graph of food intake at lunch.

FIG. 10 is a correlation between food intake and desire to eat, wherein the left graph is the placebo; the middle chart is capsaicin only; and the right chart is capsaicin and satiety drink.

DETAILED DESCRIPTION

Figure 7:
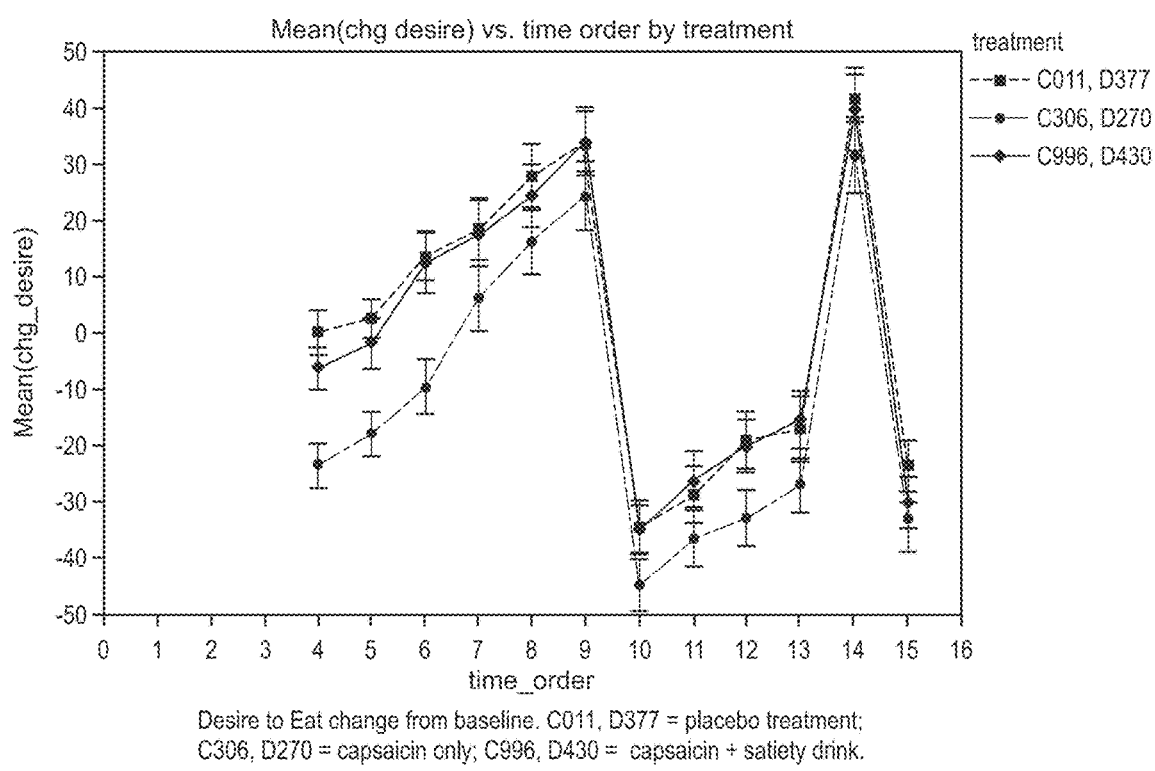
FIG. 7 is a graph of desire to eat change from baseline.

The feeling of non-absorptive satiation is mediated by the vagal nerve endings. Vagal nerve endings are specifically stimulated by cholecystokinine (CCK) as a result of the presence of food in the stomach and in the small intestine. CCK is a peptide hormone responsible for stimulating the digestion of fat and protein, and also acts as a hunger suppressant. Another effect of CCK is that it enhances the satiation response coming from the mechanical distension of the gastro-intestinal (GI) tract, typically after food intake. Vagal nerve fibers that express CCK-receptors also express the transient receptor potential cation channel subfamily V member 1 (TRPV1) receptor, also known as the capsaicin receptor. Capsaicin is the active component of chili peppers and produces a burning sensation in many tissues with which it comes into contact. Encapsulated capsaicin has the ability to stimulate the vagal nerve endings in the gastrointestinal tract.

An appetite suppressant composition having the ability to provide a feeling of pre-absorptive satiation, i.e., before energy-providing food is absorbed is described herein. An embodiment is an appetite suppressant composition having the ability to reduce body mass index, and cholesterol, triglycerides, glucose, and insulin levels. Another embodiment is an appetite suppressant composition which increases the bioavailability of the appetite suppressant composition components.

An embodiment is an appetite suppressant composition which impacts the vagal nerve endings typically activated by cholecystokinine (CCK) to generate pre-absorptive satiation. Another embodiment is an appetite suppressant composition which would increase the satiation effect of encapsulated capsaicin through a combination with material that is based on food fibers or the like which in itself results in a feeling of fullness and satiation. A flavor system that provides a delightful taste and smell, but consecutively reduces the desire for such food consumption (i.e., sensory specific satiety) is envisioned. The term "flavor system," as used herein, includes all of the flavors or flavor-enhancing components in the composition.

A composition containing an encapsulated capsaicin-based flavor system for suppressing the appetite has been developed. In one form, the appetite suppressant composition can be in the form of a snacking product, beverage, capsule, pill, lozenge, or other suitable form.

The appetite suppressant composition in one form includes encapsulated capsaicin. In an embodiment, the appetite suppressant composition can include and/or consist of at least about 0.1% (w/v) encapsulated capsaicin. Another embodiment is a method of suppressing appetite including administering an appetite suppressant composition. An embodiment relates to a method of reducing total cholesterol, glucose, insulin, and triglyceride levels including administering an appetite suppressant composition. Another embodiment relates to a method of creating a feeling of satiety including administering the appetite suppressant. One form of the composition is designed to be ingested and can be formulated into a snacking product.

As used herein, the term "capsaicin" includes natural capsaicin, capsaicinoids, and synthetic capsaicin. Capsaicin is derived from the fruits of the Solanaceae family and the *Capsicum* genus. The crude isolate of the fruit is called *capsicum* oleoresin and contains over 100 chemicals. A further extraction process results in "natural capsaicin."

As used herein, the term "natural capsaicin" contains up to 5 related molecules which are capsaicin, dihydrocapsaicin, nordihydrocapsaicin, homocapsaicin, and homodihydrocapsaicin. Most of this "natural capsaicin" is made of capsaicin and dihydrocapsaicin. "Capsaicin," also known as N-(4-hydroxy-3-methoxybenzyl)-8-methylnon-6-enamide or trans-8-Methyl-N-vanillylnon-6-enamide, has CAS Registry Number 404-86-4 and Molecular Formula: $C_{18}H_{27}NO_3$. Capsaicin has a molecular weight of 305.41 g/mol$^{-1}$. "Dihydrocapsaicin," also known as N-[(4-Hydroxy-3-methoxy-phenyl) methyl]-8-methyl-nonanamide, has CAS Registry Number 19408-84-5 and Molecular Formula $C_{18}H_{29}NO_3$. Dihydrocapsaicin has a molecular weight of 307.43 g/mol$^{-1}$.

As used herein, the term "capsaicinoids" includes compounds with action like capsaicin. These include natural and synthetic products. An example is Nonivamide (N-[(4-hydroxy-3-methoxyphenyl)methyl]nonanamide), also known as Pelargonic acid vanillylamide (PAVA), which has CAS Registry Number 2444-46-4 and Molecular Formula $C_{17}H_{27}NO_3$. Nonivamide has a molecular weight of 293.4 g/mol$^{-1}$. Also envisioned are capsinoids such as capsiate, dihydrocapsiate, nordihydrocapsiate, palvanil, etc.

"Synthetic capsaicin" can be manufactured synthetically. It can be sold as a capsaicin substitute, as it also affects the capsaicin-sensitive primary afferent fibers just like capsaicin.

Other ingredients which have similar functions to capsaicin, such as allyl isothiocyanate (the compound responsible for the pungent taste of mustard, horseradish, and wasabi), piperine (the compound responsible for the pungency of black and white pepper), and ginger (a mixture of zingerone, shogaols, and gingerols) can be encapsulated as well. Similarly, caffeine may be co-encapsulated along with capsaicin or ingredients which have similar functions to capsaicin.

In one embodiment, the snacking product containing a flavor system which stimulates the vagal nerve endings in the gastrointestinal tract providing pre-absorptive satiation is an energy drink, energy bar, or dietary supplement.

As used herein, the term "dietary supplement" refers to a supplement suitable for oral consumption that is administered orally. In preferred embodiments, the dietary supplement is in the form of capsules (e.g., those meant to be swallowed or chewed), tablets (e.g., those meant to be swallowed or chewed), powders (e.g., the powder can be added to water, milk, or another liquid), liquids (e.g., either in ready to drink form or suitable for dilution in another beverage), or nutritional foodstuffs. For example, the dietary supplement can be in the form of nutritional bars (e.g., meal or snack bars), cookies, candies (e.g., taffies, caramels, jellies, chocolate melt-aways, chews such as fruit chews, gums), syrups, or beverages (e.g., ready to drink or in the form of concentrates or powders).

The effect of the components of the appetite suppressant composition in one form are believed to immediately produce and provide a feeling of pre-absorptive satiation, i.e., before energy-providing food is absorbed. The appetite suppressant composition in one form is also believed to reduce body mass index, and cholesterol, triglycerides, blood glucose, and insulin levels.

The appetite suppressant composition further is believed to impact the TRPV1 receptors at vagal nerve endings that are also sensitive to CCK in the gastrointestinal tract. The encapsulation of capsaicin avoids the burning sensation in the mouth which may be objectionable to some consumers. The capsules dissolve in the acidic environment of the stomach but not mechanically through chewing. This allows release of the capsaicin directly into the small intestine. Once in the small intestine, capsaicin activates TRPV1 receptors at vagal nerve endings.

The capsaicin product may be coated or encapsulated. The coating or encapsulation may be performed such that the coated or encapsulated capsaicin product comprises a micro-sized spherical particle. For example, according to certain embodiments, the coated or encapsulated capsaicin product may comprise micro-sized spherical particles having a size range of 125 microns to 400 microns. The material used to coat or encapsulate the capsaicin product may comprise a digestible matrix that is degraded in the digestive and/or intestinal tract of the individual after the composition is orally consumed by the individual. In certain embodiments, the material used to coat or encapsulate the capsaicin product may comprise a hydrogenated vegetable oil matrix, a hydroxypropyl methyl cellulose, or a combination thereof. According to other embodiments, the capsaicin product may be coated or encapsulated by coating or encapsulating the capsaicin product with a hydrogenated vegetable oil matrix or granulated with the hydroxypropyl methyl cellulose. Enteric coating, sustained release coating, and inclusion complex formation may also be used. The coating or encapsulation of the capsaicin product may enable a consumer to avoid an objectionable burning sensation in the mouth.

A second component that would increase the satiation effect of encapsulated capsaicin would be the combination with material that is based on food fibers or the like which in itself results in a feeling of fullness and satiation.

A third component would be the presence of a flavor system that provides a delightful taste and smell, but consecutively reduces the desire for such food consumption (sensory specific satiety). All these components could be incorporated into the snacking product that should and could have zero or near zero calories.

In one embodiment, the appetite suppressant composition can include about 0.01% to 10% (w/v) capsaicin. In another embodiment, the appetite suppressant composition can include about 0.05% to 6% (w/v) capsaicin. The appetite suppressant composition can still further include about 0.1% to 1.5% (w/v) capsaicin. In another embodiment, the appetite suppressant composition can include at least about 0.1% (w/v) capsaicin.

The encapsulated capsaicin may be manufactured by combining all ingredients in a form suitable for oral administration, and preferably as a capsule or tablet. The encapsulated capsaicin may be encapsulated (such as in a coating of hard gelatin) for oral administration. Such techniques are well known in the art. See, e.g., Baker, *Controlled release of biologically active agents*, John Wiley & Sons, (1986). Inert fillers may also be present in oral (e.g., capsule or tablet) form.

Administration includes not only single dosage forms, but also multiple dosage forms used in conjunction with one another. For instance, in one embodiment, the dietary supplement is a capsule (e.g., containing encapsulated capsaicin). In another embodiment, the dietary supplement is an energy drink in conjunction with encapsulated capsaicin located in a screw cap that is released upon opening of the screw cap and consumed with the energy drink.

The regimen of consumption can vary according to the form of the dietary supplement. When formulated as capsules, the encapsulated capsaicin is preferably administered one to three times a day, and preferably 45 minutes to two hours prior to any given meal. Administration of the encapsulated capsaicin controls calorie intake for a considerable period of time, including up to 12 hours into the following day. The amount of encapsulated capsaicin administered is sufficient to suppress appetite. While the oral dosage may contain from 2 mg to 5000 mg (i.e., total weight of all active ingredients), a single capsule or tablet preferably contains between 10 and 1000 mg of capsaicin, more preferably between 100 and 500 mg of capsaicin, and most preferably between 320 and 380 mg of capsaicin.

Preferably, there is oral consumption of the capsule or tablet form of dietary supplements over an extended period during the subject's lifetime, preferably daily. While benefits are obtainable after various maximum periods of use (e.g., five, ten or twenty years), it is preferred that oral consumption of the capsule or tablet form of dietary supplements continues throughout the subject's lifetime. Preferably, the dietary supplement is administered at a safe and effective amount.

The examples explained below are given by way of illustration only and should not be interpreted as constituting any limitation of the subject of the present invention.

EXAMPLES

Example 1

This example demonstrates that capsaicin activates CCK-sensitive fibers in the gastro-intestinal tract to suppress hunger and that capsaicin potentiates stomach distension as does CCK. Thus, capsaicin prevents or decreases feelings of hunger and desire to eat.

Participants performed overnight fasting starting at 10:00 p.m. and recorded their dinner intake. Participants were restricted to a limited water intake, approximately 0.5 L maximum from 9:00 am on. Four experimental conditions were tested: (1) Placebo capsule/no distension; (2) Capsaicin capsule/no distension; (3) Placebo capsule/distension; and (4) Capsaicin capsule/distension. "No distension" indicates that the capsule was taken with the specified amount of water, e.g., 50 ml water. "Placebo capsules" contained no powder. "Capsaicin capsules" contained 0.32 g of red pepper. "Distension" indicates that the capsule was taken with the specified amount of liquid beverage, e.g., 150 ml Thai basil seed drink. Thai basil seed drink is a traditional Thai weight loss instrument and is mixed with sugar, water and honey.

A Visual analogue scale (VAS) test was administered to measure the attributes of hunger, satisfaction, fullness, desire to eat, and prospective food consumption. A VAS test was administered at 11:00, 11:30, 11:45, 12:00, 12:15, 12:30, 1:00, 2:00, 3:00, and 4:00. The capsule was swallowed at 11:15 and the participants consumed a standardized lunch containing a sandwich, fruit salad, cookie, and water at 12:45. Each participant underwent four sessions, separated by at least 2 days.

Results from this study are depicted in FIGS. 1-5. FIGS. 1-5 are graphs depicting prospective food consumption, desire to eat, hunger, satiety, and fullness as measured by a visual analogue test over time. Test groups include placebo with water (pbo water), capsaicin with water (cap water), placebo with Thai basil seed drink (pbo drink), and capsaicin with Thai basil seed drink (cap drink). Capsaicin alone decreased prospective food consumption and desire to eat, and increased fullness before lunch. There was no observed effect of capsaicin alone versus placebo after lunch. The basil seed drink eliminated the capsaicin effects before lunch. Capsaicin alone and the basil seed drink alone seem to increase fullness to a similar degree but are not additive. There may be differences in prospective food consumption and desire to eat with the basil seed drink versus water after lunch.

Example 2

This example includes ground red pepper alone and in combination with PINNOTHIN™ and CLEARPROTEIN™. PINNOTHIN™ is a commercially-available dietary supplement for appetite suppression containing Korean pine nut oil which causes the release of satiety hormones such as cholecystokinin (CCK) and glucagon-like peptide 1 (GLP-1). A 2008 study demonstrated a 9% reduction in food intake after PINNOTHIN™ treatment. See, e.g., Hughes et al., *The effect of Korean pine nut oil (PinnoThin) on food intake, feeding behavior and appetite: a double-blind placebo-controlled trial*, LIPIDS HEALTH DIS 7:6 (2008). CLEARPROTEIN™ is a whey protein soluble in beverages that provides a positive effect on post-meal measures of satiety.

This study utilized a randomized, double-blinded crossover study design run at a single research center. The study was conducted at the Consumer Opinion Center (COC), Richmond, Va., by Celerion, a contract research organization.

The participants comprise adult male and female smokers, age 21-65, in good health. Up to 100 adult smokers were initially recruited for screening to assure 50 enrolled participants completed the study. Smoking history of at least 6 months of five or less cigarettes per day or non-daily smokers. Neither gender constituted more than 60% of the total number of participants.

The demographics of the study appear in the following tables:

|  | Category | N | % of Total |
| --- | --- | --- | --- |
| Gender | F | 22* | 44% |
|  | M | 28** | 56% |
| Race | White | 21 | 42% |
|  | Black | 24 | 48% |
|  | Hispanic | 1 | 2% |
|  | Other | 4 | 8% |

*2 participants only completed 1 session; 1 participant completed two sessions; 1 participant didn't return the pre-dinner and post-dinner ballot ratings
**1 participant only completed 1 session; 2 participants completed two sessions; 1 participant didn't return the pre-dinner and post-dinner ballot ratings

| AGE | N | Mean | Min | Max | Median |
| --- | --- | --- | --- | --- | --- |
| All | 50 | 33.7 | 22 | 60 | 28 |
| Females | 22 | 33.8 | 22 | 58 | 29 |
| Males | 28 | 33.6 | 23 | 60 | 27.5 |

The study was conducted in three (3) Study Sessions with only one (1) Study Session per day. Each Study Session lasted approximately 7-8 hours. There was a total of 3 Study Sessions spread over 3 non-consecutive days (no more than two (2) days per week per participant). The test samples administered in each Study Session were randomized for all participants. All Study Sessions were completed by each participant within a 3-week timeframe.

For Session One (1), participants arrived at their appointed day and time of their study session after overnight abstinence from tobacco use. The nature and purpose of the study was outlined to them. All prospective participants who agreed to participate were required to read, sign, and date the Informed Consent Form (ICF) before any study procedures are performed. The Investigator or his/her designee was available to answer any questions participants may have that Celerion staff members administering the ICF could not answer. Participants who declined to participate at this stage were thanked and asked to leave.

After signing the ICF, each participant was screened for eligibility to participate in the study by reviewing inclusion/exclusion (I/E) criteria and study restrictions and completing a Tobacco Consumption History Questionnaire and General Health Questionnaire. If participants did not meet the required screening results range for study participation, they were excused. An abbreviated review of the I/E criteria and the General Health Questionnaire was conducted prior to Sessions Two (2) and Three (3) to ensure continued eligibility for the study.

For all Study Sessions, a standardized breakfast was served and the participants were asked to complete a visual analog scale (VAS) rating ballot on a computer screen before and after the meal. The participants remained in the study room for 150 minutes, and were allowed to engage in quiet activities such as reading or watching television. Next, a test sample was administered. Participants were asked to complete the VAS rating ballot prior to test sample as well as at designated intervals following the test sample. After 120 minutes, a standardized test lunch meal was served with participants permitted to consume ad libitum until reaching fullness. Following the test meal, the participants completed several more VAS rating ballots at designated intervals prior to the session end. Participants who completed Session One (1) and qualified to participate in Sessions Two (2) and Three (3) were asked to return to continue the study.

Each participant received each of the three test samples once over the three Study Sessions in a randomized fashion.

Participants were first introduced to the study procedures and then instructed by study staff on how to perform the evaluations. This included reviewing the VAS rating ballot and instructions on how to mark their ratings on the ballot sheet.

A standardized breakfast was served to all participants at 8:00 am, and they were instructed to consume all of the breakfast within the allotted 15 minute period. VAS ratings were collected before and after eating. Following breakfast, participants remained in the study room for the next 150 minutes engaging in quiet activities such as reading, watching television or other appropriate activities. No food was permitted during this time. One (1) 8 oz. bottle of water was provided to each participant during this time.

At 11:00 am, each participant provided pre-test VAS ratings followed by administration of a test sample, which was consumed completely within a 5-minute period. The participant then completed VAS ratings ballots at 15, 30, 45, 60, and 90 minutes following test sample consumption. Quiet activities were resumed in between ballot completion intervals. One (1) 8 oz. bottle of water was permitted prior to lunch. The order of test sample presentation was randomized over the three Study Sessions for each participant.

At 1:00 pm, each participant was provided pre-meal VAS ratings followed by a standardized lunch. Each participant served themselves onto a plate from their own individual serving bowl. Participants were instructed to take as much as they like (seconds, thirds, etc.) and eat until full in the allotted 30 minute period. The serving bowl was weighed before and after eating (blinded to the participant). Any food left on the participant's plate was placed back into the serving bowl prior to weighing.

Following the lunch meal, participants provided VAS ratings every 30 minutes until 3:00 pm, at which time they went through the End of Session Evaluation. Participants were given two paper VAS ballots to take with them for recording pre- and post-dinner ratings on the evening immediately following the study session. A pre-addressed, stamped envelope was provided by Celerion for the participants to mail back their ballots.

The VAS rating ballot were presented on paper and consisted of four 100-mm continuous line scales anchored at the left and right sides with descriptors such as "Not at all" and "Very Strong." The questions on the VAS rating ballot included "How strong is your desire to eat right now?"; "How hungry do you feel?"; "How much food do you think you could eat right now?"; and "How full do you feel?" Participants were instructed to place a mark on the line for each question corresponding to their ratings. A new ballot was provided at each time point. Paper ballots were provided for participants to record their ratings before and after dinner the evenings after the Study Sessions.

All meals were provided by the study facility. Participants were asked prior to study enrollment about their willingness to consume the foods that were served during the study. The Principal Investigator or his/her designee could disqualify any participant who responded they would not eat the indicated foods. Each participant received the same breakfast at the same time of day (8:00 am). The meal consisted of a pre-packaged muffin, a banana and a bottle of orange juice. Participants were instructed to consume the entire meal within a 30 minute timeframe.

Each participant received the same lunch at the same time of day (1:00 pm). The meal consisted of pasta with marinara sauce and a bottle of water. Lunch was served in individual bowls for each participant that were weighed prior to serving (blinded to the participants). Participants were instructed to serve themselves from the bowl onto their plate and to eat as much as they want, to a feeling of comfortable fullness. The participants were required to finish the bottle of water. Participants were instructed to consume their meal within a 30 minute timeframe. Participants consumed their meal in separated areas to eliminate any influence from others around them. After the participant had finished eating, the serving bowl of food was weighed again and the total weight consumed was calculated and converted to kilocalories.

Test sample ingredients included (ingredient/supplier/catalog number): gelatin capsule/Capsuline/Size 00 Blue-Blue; Ground red pepper/Elite Spice/PR9458; Bloody Mary mix/Zing Zang; Natural/Artificial amaretto flavor/Mane/F94762; Red food coloring/McCormick; Brown food coloring/McCormick; PINNOTHIN™ TG/Stepan Lipid Nutrition; and CLEARPROTEIN™/Fonterra/Whey Protein Isolate 895. Formulations included Test Sample A, with unfilled capsules and a shot comprising 60 ml bloody mary mix, 200 mg natural/artificial amaretto flavor, 8 drops red food coloring, and 4 drops brown food coloring. Formulation of Test Sample B, with 380 mg ground red pepper filled capsules and a shot comprising 60 ml bloody mary mix, 200 mg natural/artificial amaretto flavor, 8 drops red food coloring, and 4 drops brown food coloring. Formulation of Test Sample C, with 380 mg ground red pepper filled capsules and a shot comprising 60 ml bloody mary mix, 200 mg natural/artificial amaretto flavor, 8 drops red food coloring, 4 drops brown food coloring, 5 g CLEARPROTEIN™, and 3 g PINNOTHIN™ TG.

Figure 8:
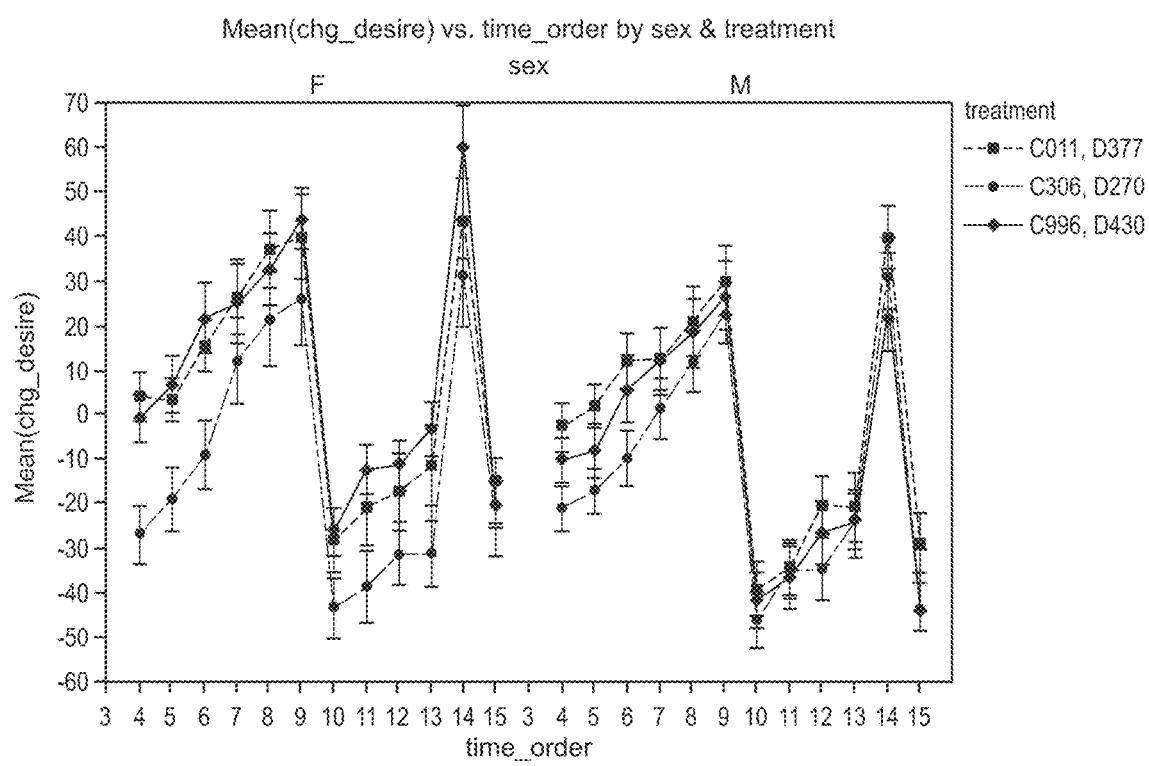
FIG. 8 is a graph of desire to eat change from the baseline separated by gender.

Results from this study are depicted in FIGS. 6-10. FIG. 6 is a distribution plot of desire to eat ratings with each point representing an individual participant. FIGS. 7 and 8 are graphs of desire to eat change from baseline and desire to eat change from baseline separated by gender. FIG. 9 is a graph of food intake at lunch separated by placebo, capsaicin only, and capsaicin plus satiety drink groups. FIG. 10 shows the correlation between food intake and desire to eat separated by placebo, capsaicin only, and capsaicin plus satiety drink groups. Capsaicin only treatment showed the greatest decrease from baseline compared to placebo for ratings of hunger, prospective food consumption, and desire to eat. PINNOTHIN™ and CLEARPROTEIN™ in combination with capsaicin was not significantly different from placebo treatment. Capsaicin only treatment effect lasted for the first hour after treatment and showed significant correlations with food intake. There was an interaction between gender and treatment for the majority of the variables, with females overall rating desire to eat and hunger lower than males for all treatments.

Example 3

Capsaicin was encapsulated in both inclusion complexes and enteric coating. Inclusion complexes of capsaicin with beta-cyclodextrin (1 g of complex containing 5 mg of capsaicin) were formed by dispersing the required amounts of beta-cyclodextrin and alcoholic solution of capsaicin in water followed by sonication. The product was recovered by drying the solid material. Enteric coatings of capsaicin were prepared by mixing the alcoholic solution of Eudragit L-100-55 polymer and capsaicin and drying into films/powders to produce encapsulated forms (1 g of product contains 5 mg of capsaicin). This product releases capsaicin in neutral pH but not in acidic pH of around 3. Other polymers such as ethyl cellulose or cellulose acetate phthalate can be used. Precipitation was performed by adding the alcoholic solution of Eudragit L-100-55 polymer and capsaicin to water. The precipitated mass was dried and ground into powder. Combinations of various polymers can be used to control the release profile of the active ingredient. Additional methods such as spray-drying may also be used. It is expected that encapsulation will increase the shelf life of the active ingredient.

While the foregoing describes in detail a zero-calorie to near-zero-calorie snacking product composition containing an encapsulated capsaicin-based flavor system with reference to specific embodiments thereof, it will be apparent to one skilled in the art that various changes and modifications equivalents to the zero-calorie to near-zero-calorie snacking product composition containing an encapsulated capsaicin-based flavor system may be employed, which do not materially depart from the spirit and scope of the invention. Accordingly, all such changes, modifications, and equivalents that fall within the spirit and scope of the invention as defined by the appended claims are intended to be encompassed thereby. All publications cited herein are incorporated by reference in their entireties for all purposes.

What is claimed is:

1. A snacking product comprising: a flavor system that comprises encapsulated capsaicin, an encapsulated capsaicin analogue, or a combination thereof; wherein the snacking product is a zero-calorie to near-zero calorie snacking product; wherein the snacking product does not comprise capsiate; and wherein the flavor system further comprises food fibers.

2. The snacking product of claim 1, wherein the snacking product is configured to stimulate vagal nerve endings in a gastrointestinal tract.

3. The snacking product of claim 2, wherein the vagal nerve endings express the transient receptor potential cation channel subfamily receptor V member 1 (TRPV1) receptor.

4. The snacking product of claim 2, wherein the vagal nerve endings express the cholecystokinin (CCK) receptor.

5. The snacking product of claim 1, wherein the encapsulated capsaicin, encapsulated capsaicin analogue, or combination thereof is micro-encapsulated.

6. The snacking product of claim 1, wherein the flavor system further comprises Korean Pine Oil.

7. The snacking product of claim 1, wherein the snacking product is an energy drink, an energy bar, a dietary supplement, a capsule, a pill, a lozenge, a sub-combination thereof or a combination thereof.

8. The snacking product of claim 1, wherein the snacking product is located in a screw cap of a beverage container.

9. The snacking product of claim 8, wherein the snacking product is released upon opening of the screw cap.

* * * * *